(12) United States Patent
Addison et al.

(10) Patent No.: US 12,369,896 B2
(45) Date of Patent: Jul. 29, 2025

(54) IMPLANT AND INTRODUCER DEVICE FOR USE IN A LUNG ACCESS PROCEDURE TO AID IN PREVENTING PNEUMOTHORAX

(71) Applicant: Bard Peripheral Vascular, Inc., Franklin Lakes, NJ (US)

(72) Inventors: Jordan Addison, Gilbert, AZ (US); Heather Storm, Phoenix, AZ (US); Koltin Glaspie, Chandler, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 645 days.

(21) Appl. No.: 17/634,343

(22) PCT Filed: Sep. 3, 2019

(86) PCT No.: PCT/US2019/049337
§ 371 (c)(1),
(2) Date: Feb. 10, 2022

(87) PCT Pub. No.: WO2021/045729
PCT Pub. Date: Mar. 11, 2021

(65) Prior Publication Data
US 2022/0280142 A1    Sep. 8, 2022

(51) Int. Cl.
*A61B 17/00*    (2006.01)

(52) U.S. Cl.
CPC ............ *A61B 17/0057* (2013.01); *A61B 2017/00004* (2013.01); *A61B 2017/00637* (2013.01)

(58) Field of Classification Search
CPC .... A61B 2017/0427; A61B 2017/0412; A61B 2017/0409; A61B 2017/0401;
(Continued)

(56) References Cited

U.S. PATENT DOCUMENTS 4,890,612 A    1/1990  Kensey
5,322,501 A *  6/1994  Mahmud-Durrani ........................ A61M 25/04
606/108

(Continued)

FOREIGN PATENT DOCUMENTS

CN    104510543 A    4/2015
CN    106413601 A    2/2017
(Continued)

OTHER PUBLICATIONS

First Office Action and Translation of First Office for Appln. No. 201980099939.9 dated May 7, 2024, 19 pages.
(Continued)

*Primary Examiner* — Jocelin C Tanner
(74) *Attorney, Agent, or Firm* — Dinsmore & Shohl LLP (57) ABSTRACT

An implant for use in a lung access procedure to aid in preventing pneumothorax includes a tubular body that has a lumen, a proximal end, and a distal end portion that terminates at a distal end. The tubular body has a longitudinal axis and has a side wall that radially surrounds the lumen. The side wall has an exterior surface. An anchor member is connected to the tubular body, wherein the anchor member is movable relative to the tubular body from a collapsed state to a deployed state. At least one suture is connected to the tubular body, wherein the at least one suture extends in a proximal direction from the proximal end of the tubular body.

20 Claims, 8 Drawing Sheets

(58) Field of Classification Search
CPC ........... A61B 2017/00809; A61B 2017/00663;
A61B 2017/00637; A61B 2017/00004;
A61B 17/00579; A61B 17/00575; A61B
17/0057; A61B 10/02; A61M 2039/0252;
A61M 39/0247
USPC ........................................................ 606/213
See application file for complete search history.

(56) References Cited

U.S. PATENT DOCUMENTS

| | | | |
|---|---|---|---|
| RE34,866 E | 2/1995 | Kensey et al. | |
| 6,174,323 B1 | 1/2001 | Biggs et al. | |
| 6,599,311 B1 | 7/2003 | Biggs et al. | |
| 6,997,189 B2 | 2/2006 | Biggs et al. | |
| 7,533,671 B2 | 5/2009 | Gonzalez et al. | |
| 7,691,151 B2 | 4/2010 | Kutsko et al. | |
| 7,931,641 B2 | 4/2011 | Chang et al. | |
| 8,252,003 B2 | 8/2012 | Tanaka et al. | |
| 8,709,034 B2 | 4/2014 | Keast et al. | |
| 8,734,362 B2 | 5/2014 | Boyle, Jr. | |
| 8,834,496 B2 | 9/2014 | Ferree | |
| 9,993,306 B2 | 6/2018 | Keast et al. | |
| 2004/0002735 A1* | 1/2004 | Lizardi | A61F 2/0811 606/232 |
| 2006/0106422 A1* | 5/2006 | Del Rio | A61B 17/0401 606/232 |
| 2006/0200177 A1 | 9/2006 | Manzo | |
| 2007/0123798 A1 | 5/2007 | Rahamimov | |
| 2009/0024149 A1* | 1/2009 | Saeed | A61B 17/0401 606/151 |
| 2009/0287229 A1* | 11/2009 | Ogdahl | A61F 2/0063 606/232 |
| 2011/0021881 A1 | 1/2011 | Wenchell et al. | |
| 2011/0112550 A1* | 5/2011 | Heaven | A61B 17/0401 606/151 |
| 2016/0206295 A1 | 7/2016 | Kramer et al. | |
| 2019/0099197 A1 | 4/2019 | Boyle, Jr. et al. | |

FOREIGN PATENT DOCUMENTS

| | | |
|---|---|---|
| CN | 108024827 A | 5/2018 |
| WO | 9912480 A1 | 3/1999 |
| WO | 2008055197 A2 | 5/2008 |
| WO | 2015168387 A2 | 11/2015 |
| WO | 2020138019 A1 | 7/2020 |

OTHER PUBLICATIONS

Japanese Office Action dated Jul. 6, 2023 pertaining to Japanese application No. 2022-514175 filed Mar. 2, 2022, pp. 1-8.
Chinese Office Action for Appln. No. 20198009939.9 mailed Oct. 26, 2024, 22 pages.

* cited by examiner

Fig. 17

IMPLANT AND INTRODUCER DEVICE FOR USE IN A LUNG ACCESS PROCEDURE TO AID IN PREVENTING PNEUMOTHORAX

CROSS-REFERENCE TO RELATED APPLICATIONS

This application is a U.S. National Phase of International Application No. PCT/US2019/049337, entitled "IMPLANT AND INTRODUCER DEVICE FOR USE IN A LUNG ACCESS PROCEDURE TO AID IN PREVENTING PNEUMOTHORAX" and filed Sep. 3, 2019, which is incorporated herein by reference in its entirety.

TECHNICAL FIELD

The present invention relates to a lung access procedure, such as a lung biopsy, and, more particularly, to an implant and introducer device for use in a lung access procedure to aid in preventing pneumothorax.

BACKGROUND ART

Pneumothorax is a problematic complication of the lung biopsy procedure where air or fluid is allowed to pass into the pleural space as a result of the puncture of the parietal pleura and visceral pleura. Pneumothorax and, more so, pneumothorax requiring chest tube placement, are significant concerns for clinicians performing, and patients undergoing, percutaneous lung biopsies. The incidence of pneumothorax in patients undergoing percutaneous lung biopsy has been reported to be anywhere from 9-54%, with an average of around 15%. On average, 6.6% of all percutaneous lung biopsies result in pneumothorax requiring a chest tube to be placed, which results in an average hospital stay of 2.7 days.

Factors that increase the risk of pneumothorax include increased patient age, obstructive lung disease, increased depth of a lesion, multiple pleural passes, increased time that an access needle lies across the pleura, and traversal of a fissure. Pneumothorax may occur during or immediately after the procedure, which is why typically a CT scan of the region is performed following removal of the needle. Other, less common, complications of percutaneous lung biopsy include hemoptysis (coughing up blood), hemothorax (a type of pleural effusion in which blood accumulates in the pleural cavity), infection, and air embolism.

What is needed in the art is an implant that may be inserted into the chest wall of a patient via an introducer device, wherein the implant has the ability to mechanically produce an airtight seal between the pleura layers prior to a lung biopsy procedure, so as to prevent pneumothorax throughout the lung biopsy procedure.

SUMMARY OF INVENTION

The present invention provides an implant that may be inserted into the chest wall of a patient via an introducer device, wherein the implant has the ability to mechanically produce an airtight seal between the pleura layers prior to a lung biopsy procedure, so as to prevent pneumothorax throughout the lung biopsy procedure.

In general, a method of the present invention involves deploying an implant having one or more proximally extending sutures. The implant is positioned on, or in, a coaxial introducer, e.g., a coaxial needle, and the coaxial needle carrying the implant is inserted through the chest wall and pleura layers to produce an access opening. The implant has one or more sutures that extend back out through the access opening to the surface of the patient's skin. Once the coaxial needle enters into the lung parenchyma, the implant is deployed and the sutures attached to the implant are pulled back so that in turn a back edge and/or surface of the implant is pulled back to force the visceral pleura up against the parietal pleura in a region around the access opening, thereby mechanically sealing the pleura layers together. The sutures are then secured in place on the patient's skin surface, e.g., by tape, adhesive, or suturing, so as to maintain the airtight seal between the parietal pleura and the visceral pleura, and the lung access procedure may be carried out.

The invention in one form is directed to an implant for use in a lung access procedure to aid in preventing pneumothorax. The implant includes a tubular body that has a lumen, a proximal end, and a distal end portion that terminates at a distal end. The tubular body has a longitudinal axis and has a side wall that radially surrounds the lumen. The side wall has an exterior surface. An anchor member is connected to, e.g., the distal end portion, of the tubular body, wherein the anchor member is movable relative to the tubular body from a collapsed state to a deployed state. At least one suture is connected to the tubular body, wherein the at least one suture extends in a proximal direction from the proximal end of the tubular body.

The invention in another form is directed to an introducer system for use in a lung access procedure to aid in preventing pneumothorax. The introducer system includes an elongate cannula and an implant. The elongate cannula has an outer surface and a longitudinal axis. The implant is coaxial with the elongate cannula. The implant includes a tubular body that has a lumen, a proximal end, and a distal end portion that terminates at a distal end. The tubular body has a side wall that radially surrounds the lumen. The side wall has an exterior surface. A portion of the elongate cannula is slidable within the lumen of the tubular body. An anchor member is connected to the distal end portion of the tubular body, wherein the anchor member is movable relative to the tubular body from a collapsed state to a deployed state. At least one suture is connected to the tubular body, wherein the at least one suture extends in a proximal direction from the proximal end of the tubular body.

An advantage of the present invention is that the implant has the ability to mechanically produce an airtight seal between the pleura layers prior to a lung biopsy procedure.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DESCRIPTION OF EMBODIMENTS

Figure 1:
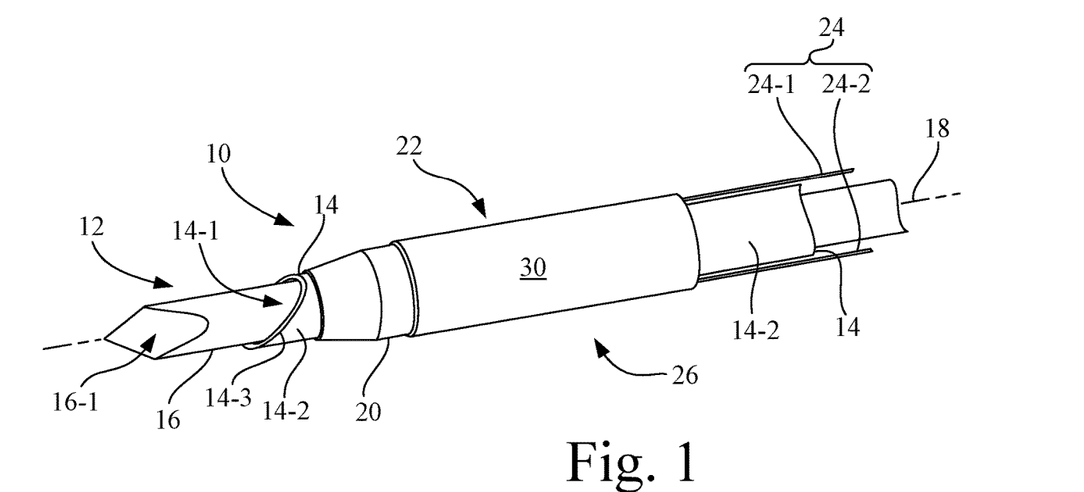
FIG. 1 is a perspective view of an introducer system having an introducer device and an implant, in accordance with an embodiment of the present invention, enlarged and with a portion of the introducer device broken away.
Figure 2:
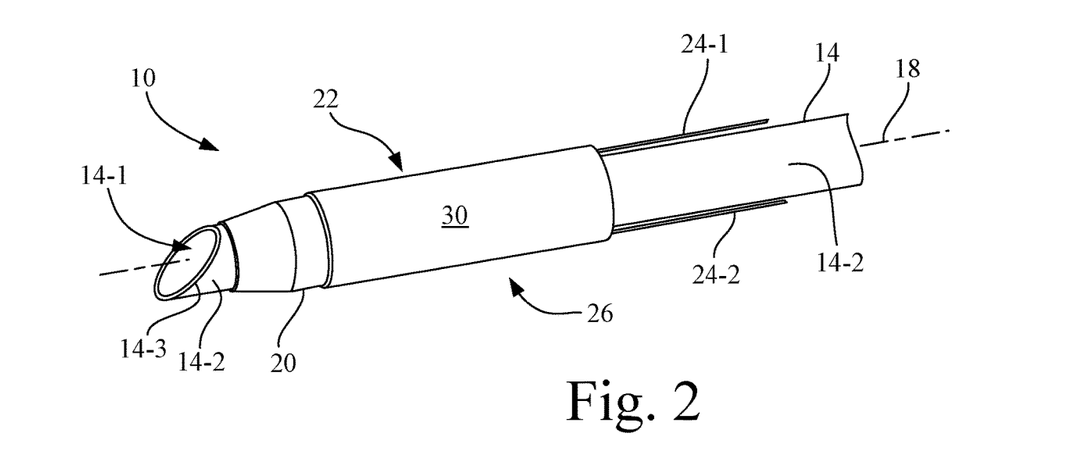
FIG. 2 is a perspective view of the implant of FIG. 1, and with the stylet removed from the elongate cannula of the introducer device of FIG. 1.

Referring now to the drawings, and more particularly to FIGS. 1 and 2, there is shown an embodiment of an implant 10 for use in a lung access procedure to aid in preventing pneumothorax, in accordance with the present invention, wherein implant 10 is shown positioned on an introducer device 12.

In the present embodiment, introducer device 12 is in the form of a coaxial arrangement of an elongate cannula 14 and a stylet 16 having a longitudinal axis 18. As best shown in FIG. 2, elongate cannula 14 has a lumen 14-1, an outer surface 14-2, and a beveled distal end 14-3. As shown in FIG. 1, stylet 16 may be in the form of an elongate trocar having a piercing tip portion 16-1. Stylet 16 is slidably received in lumen 14-1 of elongate cannula 14, and is sized such that piercing tip portion 16-1 extends distally beyond beveled distal end 14-3 of elongate cannula 14. Piercing tip portion 16-1 may include a plurality of hollow ground surfaces that distally terminate at a pointed tip.

Figure 3:
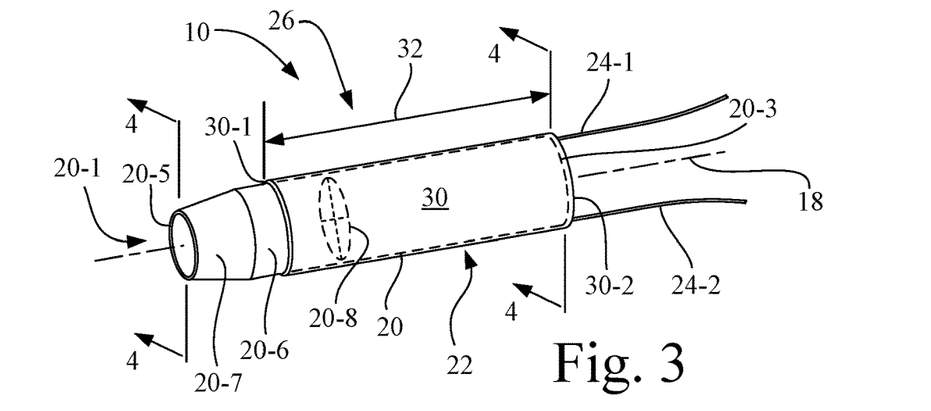
FIG. 3 is a perspective view of the implant of FIG. 1, with a portion of the tubular body that is covered by the anchor sleeve, and valve, being depicted by dashed lines.
Figure 4:
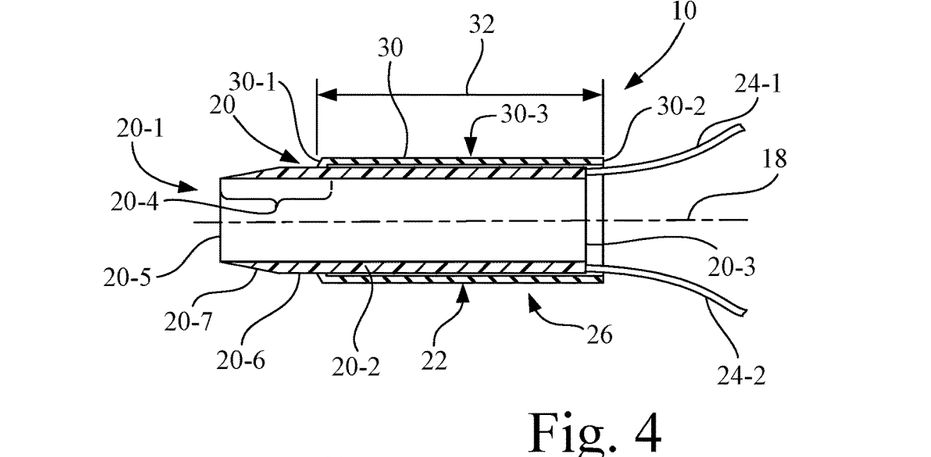
FIG. 4 is a section view of the implant of FIG. 3, taken along plane 4-4-4-4 of FIG. 3.
Figure 5:
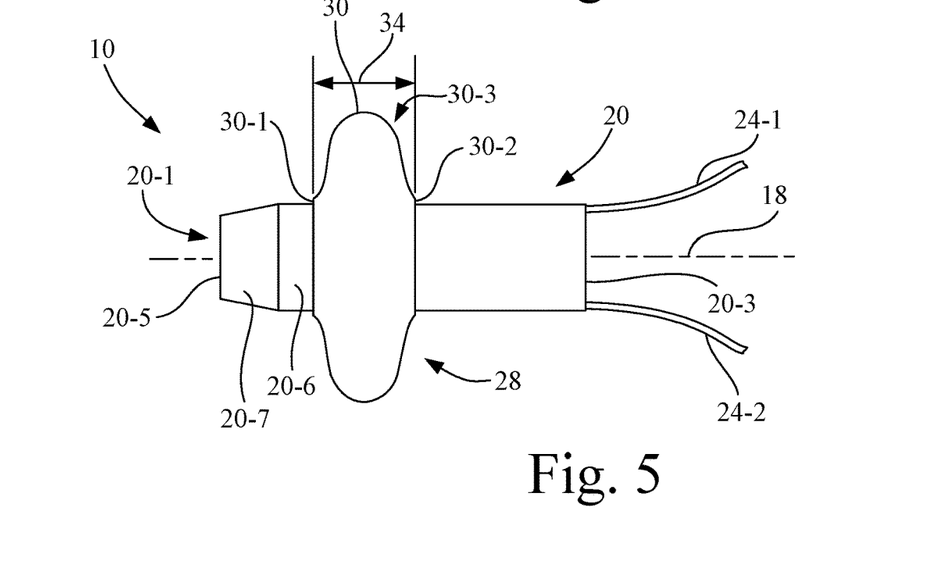
FIG. 5 is a side view of the implant of FIG. 3 shown in a deployed state, with the anchor sleeve forming a bulge.

Referring also to FIGS. 3-5, implant 10 includes a tubular body 20, an anchor member 22, and at least one suture 24. Implant 10 may be made, in whole or in part, of a fully bioabsorbable material, such as a bioabsorbable and biocompatible polymer, for example, polyglycolic acid, polylactic acid, or polydioxanone. Alternatively, at least tubular body 20 of implant 10 may be made from a non-bioabsorbable biocompatible material, such as for example, stainless steel, nitinol, or polypropylene.

In the present embodiment, there is a plurality of sutures, e.g., two or more sutures, which are individually identified as suture 24-1 and suture 24-2. Each of the sutures 24-1, 24-2 is made of thread-like material, and may be made from an absorbable material, e.g., polyglycolic acid, polylactic acid, monocryl, and polydioxanone, or may be made from a non-absorbable material, such as nylon, polyester, polyvinylidene difluoride, and polypropylene.

Tubular body 20 of implant 10 includes a lumen 20-1, a side wall 20-2, a proximal end 20-3, and a distal end portion 20-4 that terminates at a distal end 20-5. Side wall 20-2 has an exterior surface 20-6. In the present embodiment, distal end portion 20-4 of tubular body 20 includes a surface, e.g., an annular ramp surface 20-7, which tapers toward distal end 20-5. Annular ramp surface 20-7 distally terminates at lumen 20-1 of tubular body 20. Stated differently, annular ramp surface 20-7 distally terminates at distal end 20-5 of tubular body 20.

Referring to FIG. 3, in some embodiments, a valve 20-8 (e.g., a flap or membrane) may be located in lumen 20-1 of tubular body 20, so as to close off lumen 20-1 when introducer device 12 is removed from lumen 20-1.

When installed on introducer device 12, tubular body 20 is coaxial with elongate cannula 14 and stylet 16 along longitudinal axis 18. Side wall 20-2 radially surrounds lumen 20-1, and in turn, radially surrounds outer surface 14-2 of elongate cannula 14. In the present embodiment, lumen 20-1 of tubular body 20 is sized to slidably receive outer surface 14-2 of elongate cannula 14 in a snug sliding fit, i.e., a sliding friction fit, wherein side wall 20-2 of tubular body 20 of implant 10 engages outer surface 14-2 of elongate cannula 14 in a slidable friction. As such, implant 10 is configured to separate from elongate cannula 14 post-deployment. If desired, an outer cannula (not shown) may be received over elongate cannula 14 to engage proximal end 20-3 of tubular body 20, so as to aid in the insertion of implant 1 into the patient.

Figure 6:
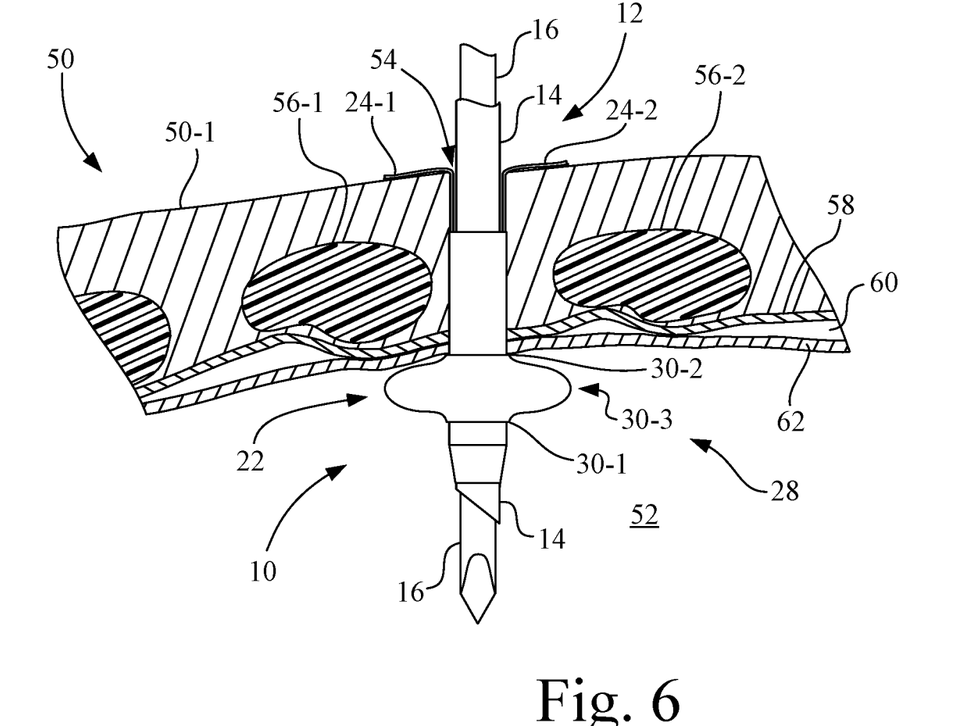
FIG. 6 depicts a section view of a portion of a chest wall and lung of a patient, and shows a side view the introducer device and implant of FIGS. 1-5 positioned in the chest wall and lung, with the implant shown in the deployed state and with the implant pulled back to mechanically seal the pleura layers.

Anchor member 22 is connected to distal end portion 20-4 of tubular body 20, wherein the anchor member 22 is movable relative to the tubular body 20 from a collapsed state 26, depicted in FIGS. 1-4, to a deployed state 28, depicted in FIGS. 5 and 6. When anchor member 22 is in the deployed state 28, at least a portion of anchor member 22 extends radially outwardly, i.e., forms a bulge, from the exterior surface 20-6 of side wall 20-2.

In the present embodiment, anchor member 22 includes a sleeve 30 that radially surrounds side wall 20-2 of tubular body 20. Sleeve 30 has a first end 30-1, a second end 30-2, and a central portion 30-3 between first end 30-1 and second end 30-2. Sleeve 30 is made from a flexible material, such as a flexible rubber or polymer material, or a mesh material, with the material forming the side wall of sleeve 30 having a thickness that is thin enough to facilitate bulging and/or bunching when implant 10 is moved in a proximal direction and the second end 30-2 of sleeve 30 engages an obstruction, e.g., the visceral pleura, as described in more detail below.

First end 30-1 of sleeve 30 is attached to the exterior surface 20-6 of side wall 20-2 of tubular body 20. Second end 30-2 of sleeve 30 is slidable over the exterior surface 20-6 of side wall 20-2 of tubular body 20, wherein in the collapsed state 26, sleeve 30 has a first longitudinal length 32 (see FIG. 4), and in the deployed state 28 (see FIG. 5), sleeve 30 has a second longitudinal length 34 that is shorter than the first longitudinal length 32. In the deployed state 28 depicted in FIGS. 5 and 6, central portion 30-3 of sleeve 30 bulges radially away from side wall 20-2 of tubular body 20 of implant 10.

In the present embodiment, each of the sutures 24-1, 24-2 is connected to the tubular body 20, wherein each of the sutures 24-1, 24-2 extends in a proximal direction from proximal end 20-3 of tubular body 20 of implant 10. In the present embodiment, each of sutures 24-1, 24-2 may be connected to proximal end 20-3 of tubular body 20. Sutures 24-1, 24-2 facilitate the transformation of sleeve 30 of anchor member 22 from the collapsed state (see FIGS. 1-4) to the deployed state (see FIGS. 5 and 6), i.e., bulged and/or bunched, as further described below.

Referring to FIG. 6, there is depicted a portion of a chest wall 50 and lung 52 of a patient. Introducer device 12, with implant 10 positioned on outer surface 14-2 of elongate cannula 14, is used to form an access opening 54 to the interior of lung 52. In particular, access opening 54 is formed between adjacent ribs 56-1, 56-2 in the rib cage of chest wall 50, and extends though the parietal pleura 58, the pleural space 60 and the visceral pleura 62 to provide access to the interior of the lung. Implant 10 is shown positioned in access opening 54, with the entirety of sleeve 30 of anchor member 22 being positioned in access opening 54 distal to, i.e., below, the visceral pleura 62. Each of the plurality of sutures 24-1, 24-2 extends back out through access opening 54 to the surface of the patient's skin 50-1.

Once introducer device 12 enters into the lung parenchyma, implant 10 is moved from the collapsed state to the deployed state by pulling the sutures 24-1, 24-2, wherein implant 10 is pulled back along access opening 54. When implant 10 is pulled back, second end 30-2 (i.e., the back edge and/or surface) of sleeve 30 of anchor member 22 is pulled into contact with the visceral pleura 62, and the central portion 30-3 of sleeve 30 of anchor 22 begins to bulge and/or bunch, thereby increasing the contact area between the exterior of the central portion 30-3 of sleeve 30 and the visceral pleura 62. Sutures 24-1, 24-2 are further pulled, such that the bulged sleeve 30 forces the visceral pleura 62 up against the parietal pleura 58, thereby establishing a clamping force that mechanically seals the pleura layers 58, 62 together in a region around access opening 54. The sutures 24-1, 24-2 are then secured in place on the surface of patient's skin 50-1, e.g., by tape, adhesive, or suturing, so as to maintain the seal between visceral pleura 62 and the parietal pleura 58 in a region around access opening 54.

The lung access procedure, such as a lung biopsy, may be carried out by removing stylet 16 from elongate cannula 14, and then inserting a lung biopsy device through lumen 14-1 of elongate cannula 14 and into the lung. Alternatively, the lung access procedure may be carried out by removing the entirety of introducer device 12, and a lung biopsy device may be inserted through lumen 20-1 of tubular body 20 of implant 10 and into the lung.

Figure 7:
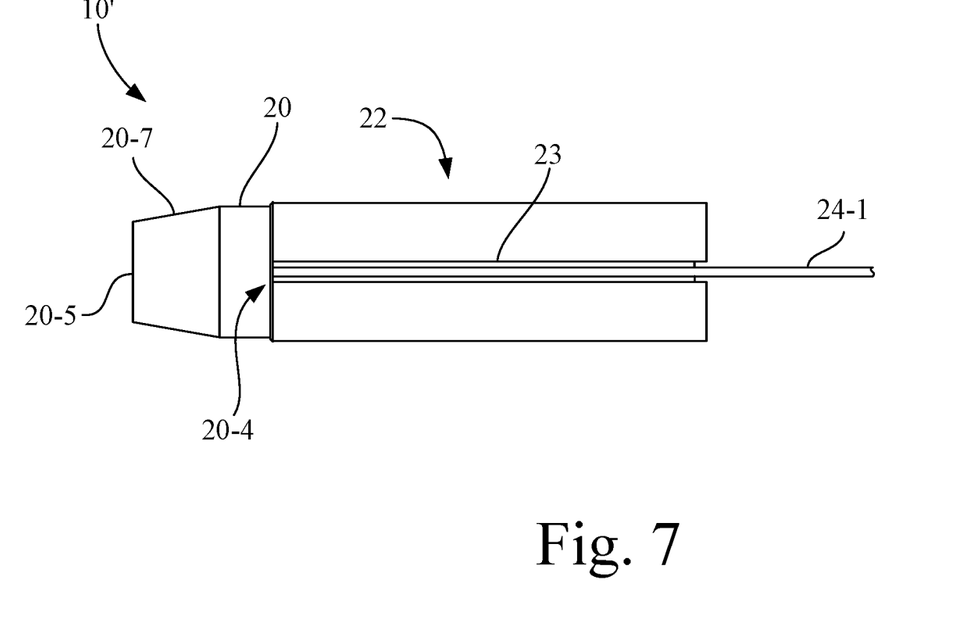
FIG. 7 is a side view of an alternative embodiment of the implant of FIG. 1-6.
Figure 8:
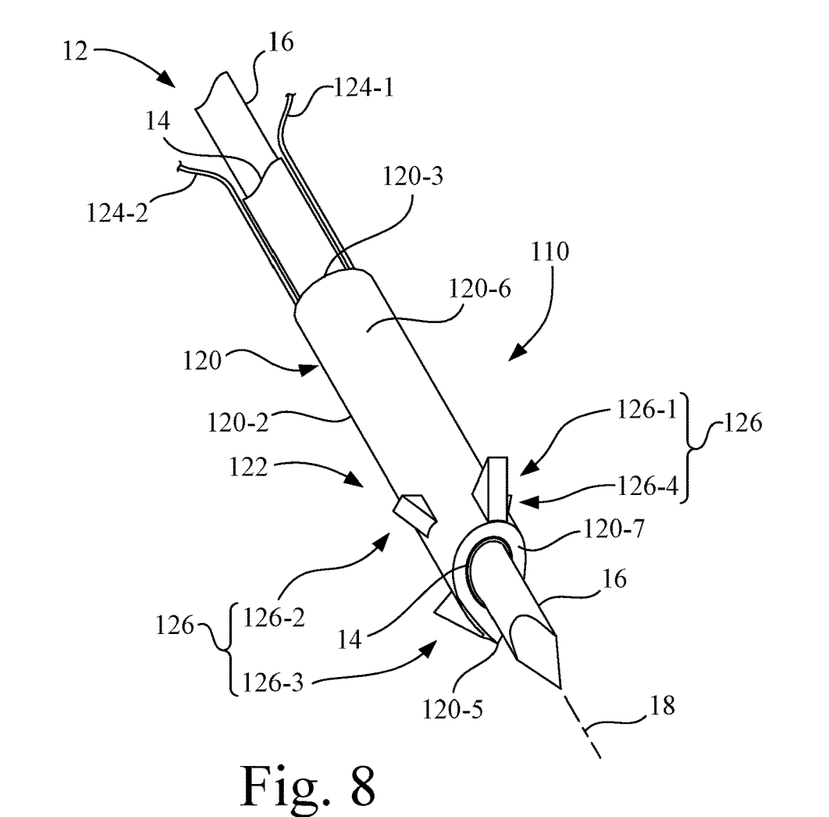
FIG. 8 is a perspective view of an introducer device having an implant in accordance with another embodiment of the present invention, enlarged and with a portion of the introducer device broken away.

FIG. 7 shows an implant 10', as a variation of implant 10. For convenience, components common to both of implant 10 and implant 10' will share the same element numbers. Implant 10' differs from implant 10 in that an anchor member 22 has a channel 23 to split the side wall of anchor member 22. The presence of channel 23 aids in the transition from the collapse state 26 (see FIGS. 1-4) to the deployed, i.e., expanded, state 28 (see FIGS. 5 and 6). Also, if desired, suture 24-1 may be positioned in channel 23, and attached to exterior surface 20-6 of tubular body 20, such as at distal end portion 20-4 of tubular body 20. It is contemplated that anchor member 22 may include two or more channels like channel 23, such as, for example, two diametrically opposed channels to respectively accommodate sutures 24-1, 24-2.

Implant 10' may be made of a fully bioabsorbable material, such as a bioabsorbable and biocompatible polymer, as described above with respect to implant 10. Alternatively, at least tubular body 20 of implant 10' may be made from non-bioabsorbable biocompatible material, as described above with respect to implant 10.

FIGS. 8-11 show another implant 110 in accordance with an aspect of the present invention, for use in a lung access procedure to aid in preventing pneumothorax, wherein implant 110 is shown positioned on introducer device 12. Introducer device 12 is described above, and for brevity will not be discussed in detail here.

Implant 110 includes a tubular body 120, an anchor member 122, and at least one suture 124. Implant 110 may be made, in whole or in part, of a fully bioabsorbable material, such as a bioabsorbable and biocompatible polymer, for example, polyglycolic acid, polylactic acid, or polydioxanone. Alternatively, at least tubular body 120 of implant 110 may be made from non-bioabsorbable biocompatible material, such as for example, stainless steel, nitinol, or polypropylene.

In the present embodiment, there is a plurality of sutures, e.g., two or more sutures, which are individually identified as suture 124-1 and suture 124-2. Each of the sutures 124-1, 124-2 is made of thread-like material, and may be made from an absorbable material, e.g., polyglycolic acid, polylactic acid, monocryl, and polydioxanone, or may be made from a non-absorbable material, such as nylon, polyester, polyvinylidene difluoride, and polypropylene.

Figure 10:
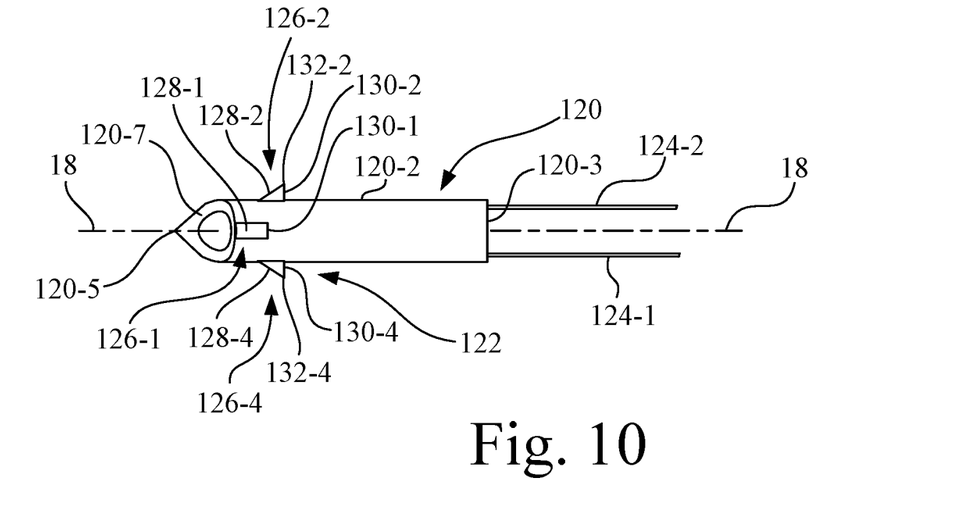
FIG. 10 is a top view of the implant of FIGS. 8 and 9.
Figure 11:
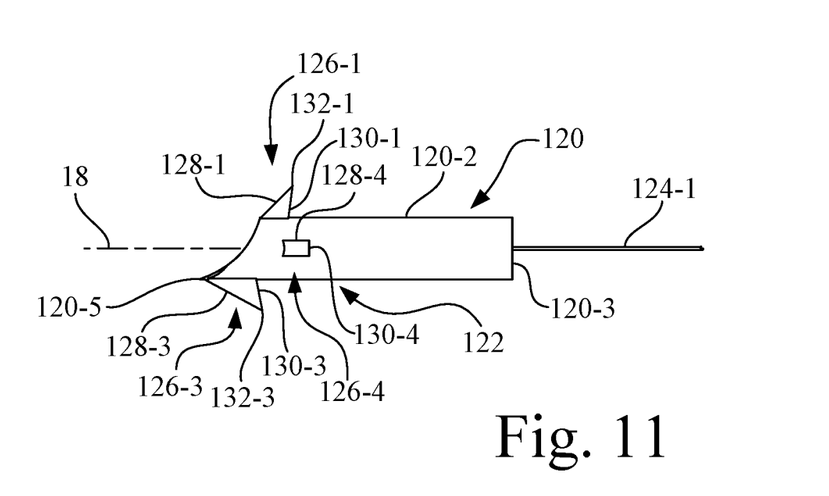
FIG. 11 is a side view of the implant of FIGS. 8 and 9.

Tubular body 120 of implant 110 includes a lumen 120-1, a side wall 120-2, a proximal end 120-3, and a distal end portion 120-4 that terminates at a distal end 120-5. Side wall 120-2 has an exterior surface 120-6. In the present embodiment, distal end portion 120-4 of tubular body 120 includes a surface, e.g., an annular ramp surface 120-7, which tapers toward distal end 120-5. Annular ramp surface 120-7 distally terminates at lumen 120-1 of tubular body 120. Stated differently, annular ramp surface 120-7 distally terminates at distal end 120-5 of tubular body 120. In the present embodiment, annular ramp surface 120-7 may be hollow ground to form a concave profile, as best shown in FIGS. 10 and 11.

Figure 9:
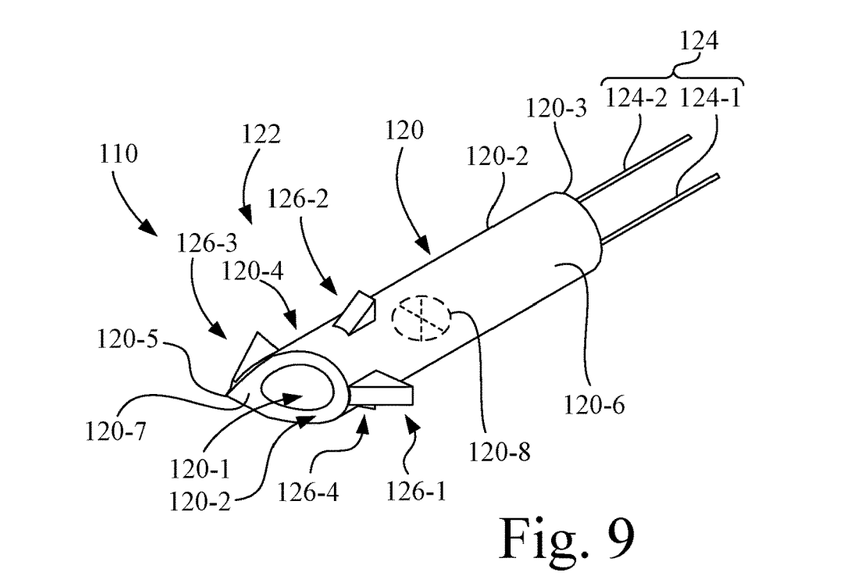
FIG. 9 is a perspective view of the implant of FIG. 8.

Referring to FIG. 9, in some embodiments, a valve 120-8 (e.g., a flap or membrane) may be located in lumen 120-1 of tubular body 120, so as to close off lumen 120-1 when introducer device 12 is removed from lumen 120-1.

When installed on introducer device 12, tubular body 120 is coaxial with elongate cannula 14 and stylet 16 along longitudinal axis 18, with lumen 120-1 of tubular body 120 sized to slidably receive and engage outer surface 14-2 of elongate cannula 14 in a snug sliding fit. Side wall 120-2 radially surrounds lumen 120-1, and in turn, radially surrounds outer surface 14-2 of elongate cannula 14.

Anchor member 122 is connected to distal end portion 120-4 of tubular body 120. In the present embodiment, anchor member 122 includes a plurality of engagement members 126 spaced apart and positioned around side wall 120-2 of tubular body 120 at distal end portion 120-4. In the present embodiment, the plurality of engagement members 126, here shown as a plurality of triangular prisms, includes individual engagement members 126-1, 126-2, 126-3, and 126-4. Referring to FIGS. 10 and 11, each engagement member, e.g., triangular prism, of the plurality of engagement members 126 has a respective ramp surface 128-1, 128-2, 128-3, 128-4 and a respective proximal surface 130-1, 130-2, 130-3, 130-4, wherein each proximal surface 130-1, 130-2, 130-3, 130-4 is substantially perpendicular to side wall 120-2 and each ramp surface 128-1, 128-2, 128-3, 128-4 extends proximally from side wall 120-2 at an acute angle with respect to side wall 120-2 to join the respective proximal surface 130-1, 130-2, 130-3, 130-4 to form a respective apex 132-1, 132-2, 132-3, 132-4. As used herein, the term "substantially perpendicular" means perpendicular and a variation from perpendicular of up to ±10 degrees.

In the present embodiment, engagement members 126-1, 126-2, 126-3, and 126-4 may be arranged in diametrically opposed pairs. Also, in the present embodiment, each of engagement members 126-1, 126-2, 126-3, and 126-4 may have a substantially right-triangle profile, with at least some of the various triangular profiles having different sizes. As such, a radial length of the respective proximal surface 130-1, 130-2, 130-3, 130-4 may differ as between some of the engagement members. Also, it is noted that the engagement members 126-1, 126-2, 126-3, and 126-4 may be longitudinally staggered along a length of side wall 120-2 of tubular body 120.

In the present embodiment, each of the sutures 124-1, 124-2 is connected to the tubular body 120, e.g., proximal end 120-3 of tubular body 120, wherein the sutures 124-1, 124-2 extend in a proximal direction from proximal end 120-3 of tubular body 120 of implant 110. Sutures 124-1, 124-2 facilitate longitudinal movement of implant 110 in a proximal direction, i.e., toward the user, when pulled.

Figure 12:
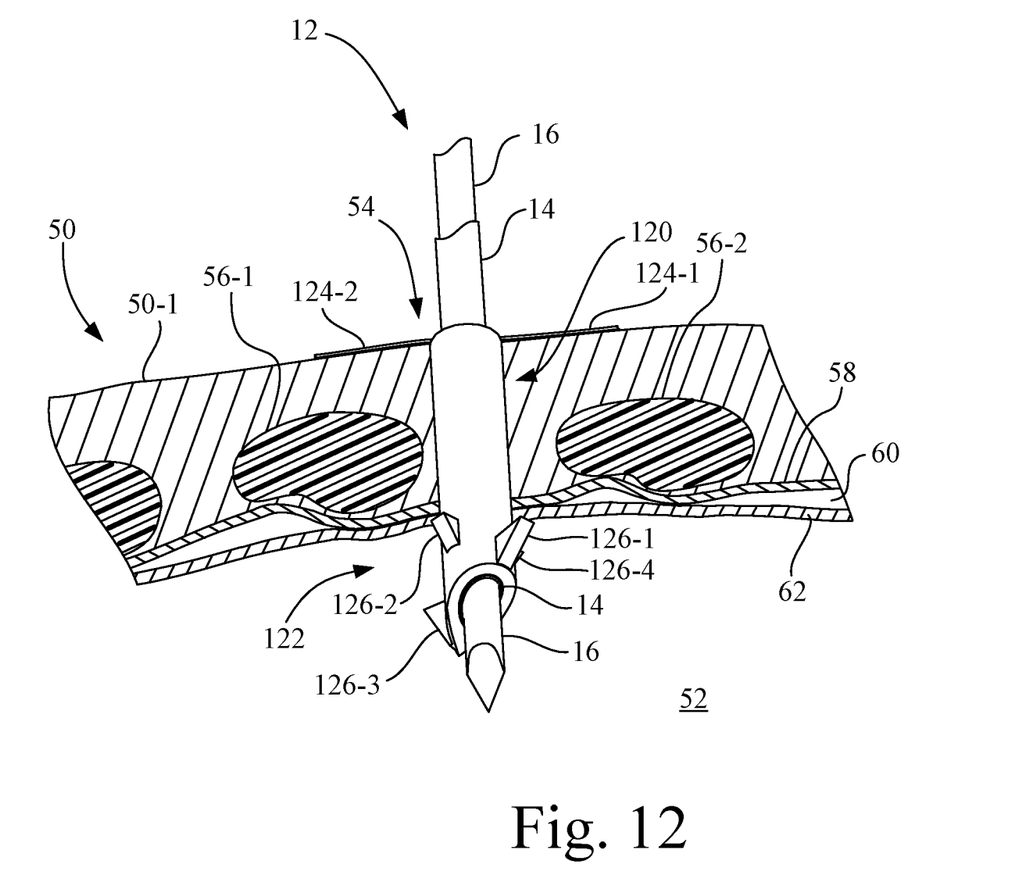
FIG. 12 depicts a section view of a portion of a chest wall and lung of a patient, and shows a perspective view of the introducer device and implant of FIG. 8 positioned in the chest wall and lung, with the implant pulled back to mechanically seal the pleura layers.

Referring to FIG. 12, there is depicted a portion of a chest wall 50 and lung 52 of a patient, including access opening 54 formed between adjacent ribs 56-1, 56-2 in the rib cage of chest wall 50, and which extends though the parietal pleura 58, the pleural space 60 and the visceral pleura 62 to provide access to the interior of the lung. Implant 110 is shown positioned in access opening 54, with the entirety of anchor member 122 being positioned in access opening 54 below the visceral pleura 62. The plurality of sutures 124-1, 124-2 extend back out through the access opening 54 to the surface of the patient's skin 50-1.

Once introducer device 12 enters into the lung parenchyma, implant 110 is moved in a proximal direction by pulling the sutures 124-1, 124-2, wherein implant 110 is pulled back along access opening 54. When implant 110 is pulled back, at least some of proximal surfaces 130-1, 130-2, 130-3, 130-4 (see also FIGS. 10 and 11) of the engagement members 126-1, 126-2, 126-3, and 126-4 of anchor member 122 are pulled into contact with the visceral pleura 62. As sutures 124-1, 124-2 are further pulled, at least some of the engagement members 126-1, 126-2, 126-3, and 126-4 of anchor member 122 force the visceral pleura 62 up against the parietal pleura 58, thereby establishing a clamping force to mechanically seal the pleura layers 58, 62 together in a region around access opening 54. The sutures 124-1, 124-1 are then secured in place on the surface of patient's skin 50-1, e.g., by tape, adhesive, or suturing, so as to maintain the seal between visceral pleura 62 and the parietal pleura 58 in a region around access opening 54.

The lung access procedure, such as a lung biopsy, may be carried out by removing stylet 16 from elongate cannula 14, and then inserting a lung biopsy device through lumen 14-1 of elongate cannula 14 and into the lung. Alternatively, the lung access procedure may be carried out by removing the entirety of introducer device 12, and a lung biopsy device may be inserted through lumen 120-1 of tubular body 120 of implant 110 and into the lung.

Figure 13:
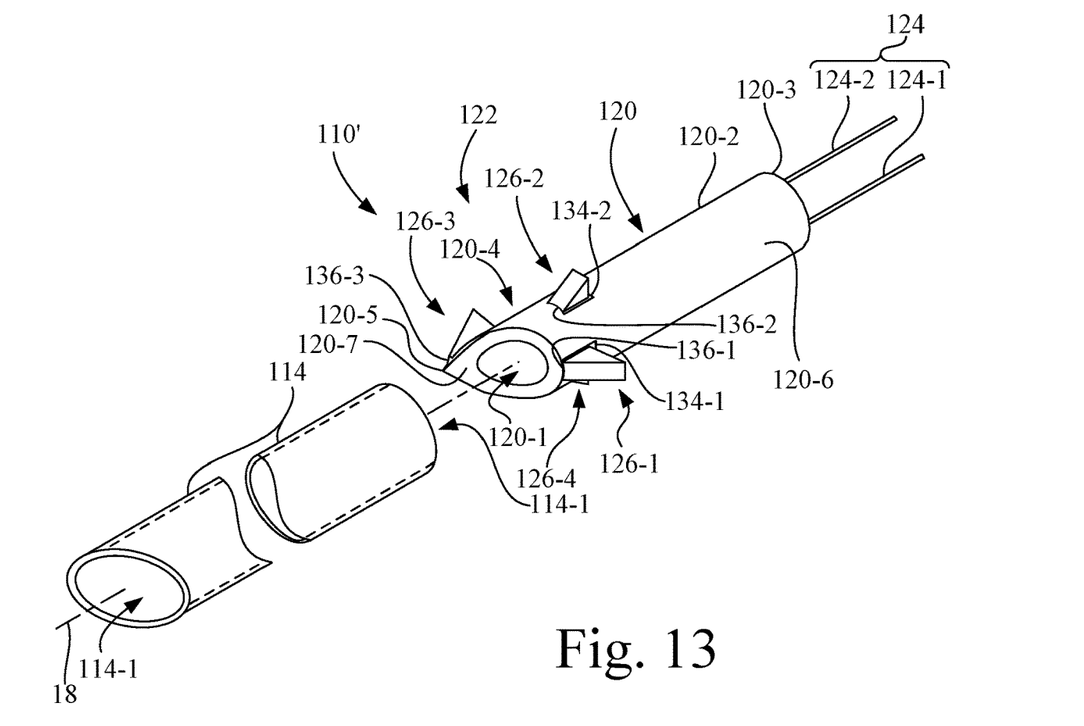
FIG. 13 is a perspective view of an implant in accordance with another embodiment of the present invention, to be received in an outer cannula to collapse a retractable anchor member having a plurality of retractable engagement members.
Figure 14:
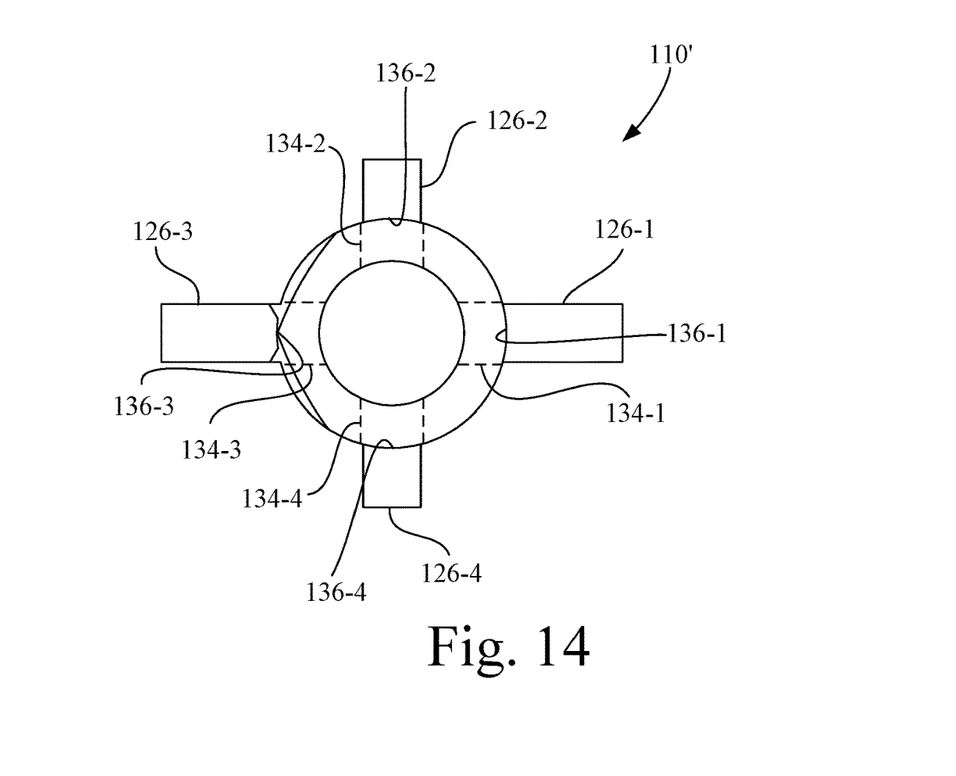
FIG. 14 is a front view of the implant of FIG. 13, with the retraction slots of the tubular body depicted by dashed lines.

FIGS. 13 and 14 show an implant 110' as a variation of implant 110 of FIGS. 8-12. For convenience, components common to both of implant 110 and implant 110' will share the same element numbers. Implant 110' differs from implant 110 in that each of engagement members 126-1, 126-2, 126-3, and 126-4 of anchor member 122 is made to retract into a slot when acted upon by an outside force, e.g., inserted into the lumen 114-1 of an outer cannula 114.

In the embodiment of FIGS. 13 and 14, side wall 120-2 of tubular body 120 includes a plurality of longitudinal slots 134-1, 134-2, 134-3, and 134-4 that radially extend from exterior surface 120-6 to lumen 120-1 of tubular body 120. Each of the plurality of engagement members 126-1, 126-2, 126-3, and 126-4 includes a distal hinge 136-1, 136-2, 136-3, 136-4, respectively, e.g., made of a memory material, that connects the respective engagement member to tubular body 120. Each longitudinal slot of the plurality of longitudinal slots 134-1, 134-2, 134-3, and 134-4 is configured to radially receive a respective engagement member of the plurality of engagement members 126-1, 126-2, 126-3, and 126-4 of anchor member 122.

When implant 110' is inserted into lumen 114-1 of outer cannula 114, each of the plurality of engagement members 126-1, 126-2, 126-3, and 126-4 pivots at its respective distal hinge 136-1, 136-2, 136-3, 136-4 and is retracted into a respective longitudinal slot of the plurality of longitudinal slots 134-1, 134-2, 134-3, and 134-4. When implant 110' is removed from lumen 114-1 of outer cannula 114, e.g., by being pushed by a pushrod, each of the plurality of engagement members 126-1, 126-2, 126-3, and 126-4 pivots at its respective distal hinge 136-1, 136-2, 136-3, 136-4 to return to an extended position, i.e., to radially extend outwardly from the respective longitudinal slot of the plurality of longitudinal slots 134-1, 134-2, 134-3, and 134-4.

Figure 15:
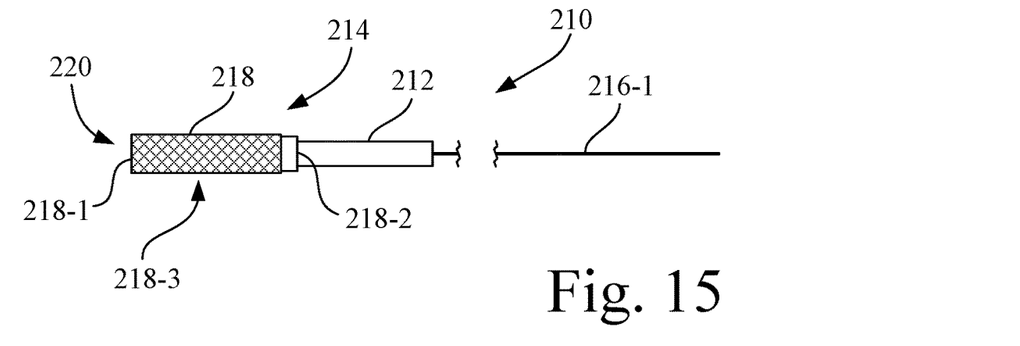
FIG. 15 is a side view of an implant in accordance with another embodiment of the present invention, with the implant being in a collapsed state.
Figure 16:
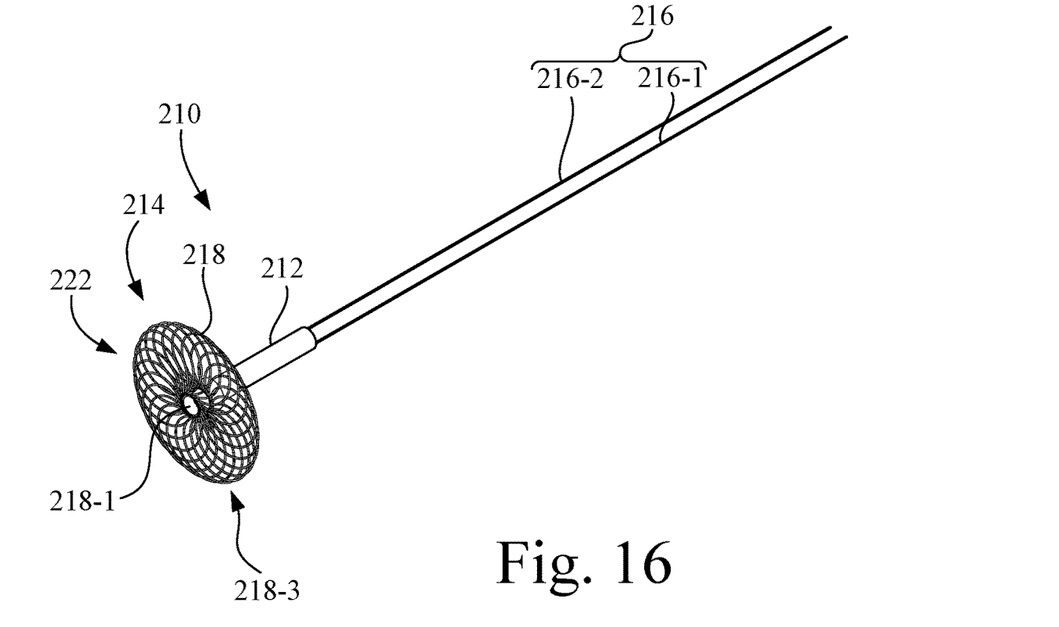
FIG. 16 is a perspective view of the implant of FIG. 15, with the implant being in a deployed state.
Figure 17:
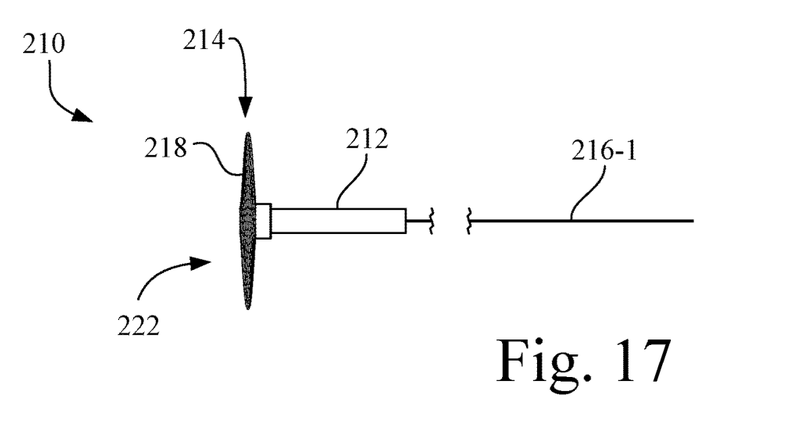
FIG. 17 is a side view of the implant of FIG. 15, with the implant being in the deployed state.

Referring to FIGS. 15-17, there is shown an implant 210 in accordance with another embodiment of the present invention.

Implant 210 includes a tubular body 212, an anchor member 214, and at least one suture 216. Implant 210 may be made of a fully bioabsorbable material, such as a bioabsorbable and biocompatible polymer, for example, polyglycolic acid, polylactic acid, or polydioxanone. Alternatively, implant 210 may be made, in whole or in part, from non-bioabsorbable biocompatible material, such as for example, stainless steel, nitinol, or polypropylene.

In the present embodiment, there is a plurality of sutures, e.g., two or more sutures, which are individually identified as suture 216-1 and suture 216-2. Sutures 216-1, 216-2 may be connected to first end 218-1 of mesh sleeve 218. Each of the sutures 216-1-1, 216-2 is made of thread-like material, and may be made from an absorbable material, e.g., polyglycolic acid, polylactic acid, monocryl, and polydioxanone, or may be made from a non-absorbable material, such as nylon, polyester, polyvinylidene difluoride, and polypropylene.

In the present embodiment, anchor member 214 includes a mesh sleeve 218 that is made from a flexible material, such as a flexible rubber or polymer material. Mesh sleeve 218 has a first end 218-1, a second end 218-2, and a central portion 218-3 between first end 218-1 and second end 218-2.

Mesh sleeve 218 is movable relative to tubular body 212 from a collapsed state 220, depicted in FIG. 15, to a deployed state 222, depicted in FIGS. 16 and 17. When mesh sleeve 218 of anchor member 214 is in the deployed state 222, at least a portion of anchor member 214 extends radially outwardly, i.e., forms a bulge. More particularly, in the deployed state 222 depicted in FIGS. 16 and 17, central portion 218-3 of mesh sleeve 218 bulges radially outwardly from tubular body 212 of implant 210.

Sutures 216-1, 216-2 extend in a proximal direction from tubular body 212 of implant 210. Sutures 216-1, 216-2 facilitate the transformation of mesh sleeve 218 of anchor member 214 from the collapsed state 222 (see FIG. 15) to the deployed, i.e., bulged, state 222 (see FIGS. 16 and 17, by axially moving first end 218-1 of mesh sleeve 218 relative to second end 218-2 of mesh sleeve 218 when sutures 216-1, 216-2 are pulled.

To facilitate deployment in a patient, implant 210 may be positioned in a lumen of an introducer cannula, such as lumen 114-1 of outer cannula 114 depicted in FIG. 13, and may be pushed out of the lumen by using a pushrod.

The following items also relate to the invention:

In one form, the invention relates to an implant for use in a lung access procedure to aid in preventing pneumothorax. The implant may include a tubular body that has a lumen, a proximal end, and a distal end portion that terminates at a distal end, and wherein the tubular body has a longitudinal axis and has a side wall that radially surrounds the lumen, the side wall having an exterior surface. An anchor member may be connected to the tubular body, wherein the anchor member may be movable relative to the tubular body from a collapsed state to a deployed state. At least one suture may be connected to the tubular body, wherein the at least one suture extends in a proximal direction from the proximal end of the tubular body.

In any of the embodiments, when the anchor member is in the deployed state, at least a portion of the anchor member may extend radially outwardly from the exterior surface of the side wall.

In some embodiments, the anchor member may include a plurality of engagement members spaced apart and positioned around the side wall of the tubular body.

In some embodiments, each engagement member of the plurality of engagement members may have a ramp surface and a proximal surface, wherein the proximal surface may be perpendicular to the side wall and the ramp surface may extend proximally from the side wall at an acute angle with respect to the side wall to join the proximal surface to form an apex.

In some embodiments, the side wall of the tubular body may include a plurality of longitudinal slots that radially extend from the exterior surface to the lumen, and wherein each longitudinal slot of the plurality of longitudinal slots may be configured to receive a respective engagement member of the plurality of engagement members.

In some embodiments, the anchor member may include a sleeve that radially surrounds the side wall, wherein the sleeve may be made from a flexible material, the sleeve having a first end and a second end, wherein the first end may be attached to the exterior surface of the side wall and the second end may be slidable over the exterior surface of the side wall, wherein in the collapsed state the sleeve has a first longitudinal length and in the deployed state the sleeve has a second longitudinal length that is shorter than the first longitudinal length.

In the embodiment described immediately above, in the deployed state, a central portion of the sleeve may bulge radially away from the side wall of the tubular body.

In any of the embodiments, the distal end portion of the tubular body may include an annular ramp surface that distally terminates at the lumen at the distal end of the tubular body.

In any of the embodiments, the distal end portion of the tubular body may include a ramp surface that distally terminates at the distal end of the tubular body.

In any of the embodiments, each of the tubular body and the anchor member may be made from a bioabsorbable material.

In another form, the invention relates to an introducer system for use in a lung access procedure to aid in preventing pneumothorax. The system may include an elongate cannula having an outer surface and a longitudinal axis. An implant may be coaxial with the elongate cannula. The implant may include a tubular body that has a lumen, a proximal end, and a distal end portion that terminates at a distal end, and wherein the tubular body has a side wall that radially surrounds the lumen, the side wall having an exterior surface, and wherein a portion of the elongate cannula may be slidable within the lumen of the tubular body. An anchor member may be connected to the distal end portion of the tubular body, wherein the anchor member may be movable relative to the tubular body from a collapsed state to a deployed state. At least one suture, and in some embodiments a plurality of sutures, may be connected to the tubular body, wherein the suture(s) extend in a proximal direction from the proximal end of the tubular body.

In any of the embodiments, when the anchor member is in the deployed state, at least a portion of the anchor member may extend radially outwardly from the exterior surface of the side wall.

In some embodiments, the anchor member may include a plurality of engagement members spaced apart and positioned around the side wall of the tubular body.

In some embodiments, each engagement member of the plurality of engagement members may have a ramp surface and a proximal surface, wherein the proximal surface may be perpendicular to the side wall and the ramp surface may extend proximally from the side wall at an acute angle with respect to the side wall to join the proximal surface to form an apex.

In some embodiments, the side wall of the tubular body may include a plurality of longitudinal slots that radially extend from the exterior surface to the lumen, and wherein each longitudinal slot of the plurality of longitudinal slots may be configured to receive a respective engagement member of the plurality of engagement members.

In some embodiments, the anchor member may include a sleeve that radially surrounds the side wall, wherein the sleeve may be made from a flexible material, the sleeve having a first end and a second end, wherein the first end may be attached to the exterior surface of the side wall and the second end may be slidable over the exterior surface of the side wall, wherein in the collapsed state the sleeve has a first longitudinal length and in the deployed state the sleeve has a second longitudinal length that is shorter than the first longitudinal length.

In the embodiment described immediately above, in the deployed state, a central portion of the sleeve may bulge radially away from the side wall of the tubular body.

In any of the embodiments, the distal end portion of the tubular body may include an annular ramp surface that distally terminates at the lumen at the distal end of the tubular body.

In any of the embodiments, the distal end portion of the tubular body may include a planar ramp surface that distally terminates at the distal end of the tubular body.

In any of the embodiments, the side wall of the tubular body of the implant may be in a friction fit with the outer surface of the elongate cannula, wherein the implant may be configured to separate from the elongate cannula.

While this invention has been described with respect to multiple embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An implant for use in a lung access procedure to aid in preventing pneumothorax, comprising:
    a stylet having a piercing tip;
    a tubular body that has a lumen, a proximal end, and a distal end portion that terminates at a distal end, and wherein the tubular body has a longitudinal axis and has a side wall that radially surrounds the lumen, the side wall having an exterior surface, the sidewall of the tubular body surrounding the stylet;
    an anchor member connected to the tubular body, wherein the anchor member surrounds the tubular body, wherein the anchor member is movable relative to the tubular body from a collapsed state to a deployed state and the anchor member includes a plurality of engagement members, and wherein each engagement member of the plurality of engagement members has a ramp surface and a proximal surface; and
    at least one suture connected to the tubular body, wherein the at least one suture extends in a proximal direction from the proximal end of the tubular body.

2. The implant according to claim 1, wherein when the anchor member is in the deployed state, at least a portion of the anchor member extends radially outwardly from the exterior surface of the side wall.

3. The implant according to claim 1, wherein the plurality of engagement members are spaced apart and positioned around the side wall of the tubular body.

4. The implant according to claim 1, wherein the proximal surface is perpendicular to the side wall and the ramp surface extends proximally from the side wall at an acute angle with respect to the side wall to join the proximal surface to form an apex.

5. The implant according to claim 3, wherein the side wall of the tubular body includes a plurality of longitudinal slots that radially extend from the exterior surface to the lumen, and wherein each longitudinal slot of the plurality of longitudinal slots is configured to receive a respective engagement member of the plurality of engagement members.

6. The implant according to claim 1, wherein the anchor member includes a sleeve that radially surrounds the side wall, wherein the sleeve is made from a flexible material, the sleeve having a first end and a second end, wherein the first end is attached to the exterior surface of the side wall and the second end is slidable over the exterior surface of the side wall, wherein in the collapsed state the sleeve has a first longitudinal length and in the deployed state the sleeve has a second longitudinal length that is shorter than the first longitudinal length.

7. The implant according to claim 6, wherein in the deployed state, a central portion of the sleeve bulges radially away from the side wall of the tubular body.

8. The implant according to claim 1, wherein the distal end portion of the tubular body includes an annular ramp surface that distally terminates at the lumen at the distal end of the tubular body.

9. The implant according to claim 1, wherein the distal end portion of the tubular body includes a ramp surface that distally terminates at the distal end of the tubular body.

10. The implant according to claim 1, wherein each of the tubular body and the anchor member is made from a bioabsorbable material.

11. An introducer system for use in a lung access procedure to aid in preventing pneumothorax, comprising:
    an elongate cannula having an outer surface and a longitudinal axis; and
    an implant that is coaxial with the elongate cannula, the implant including:
        a tubular body that has a lumen, a proximal end, and a distal end portion that terminates at a distal end, and wherein the tubular body has a side wall that radially surrounds the lumen, the side wall having an exterior surface, and wherein a portion of the elongate cannula is slidable within the lumen of the tubular body;
        an anchor member connected to the distal end portion of the tubular body, wherein the anchor member surrounds the tubular body, wherein the anchor member is movable relative to the tubular body from a collapsed state to a deployed state; and
        at least one suture connected to the tubular body, wherein the at least one suture extends in a proximal direction from the proximal end of the tubular body.

12. The introducer system according to claim 11, wherein when the anchor member is in the deployed state, at least a portion of the anchor member extends radially outwardly from the exterior surface of the side wall.

13. The introducer system according to claim 11, wherein the anchor member includes a plurality of engagement members spaced apart and positioned around the side wall of the tubular body.

14. The introducer system according to claim 13, wherein each engagement member of the plurality of engagement members has a ramp surface and a proximal surface, wherein the proximal surface is perpendicular to the side wall and the ramp surface extends proximally from the side wall at an acute angle with respect to the side wall to join the proximal surface to form an apex.

15. The introducer system according to claim 13, wherein the side wall of the tubular body includes a plurality of longitudinal slots that radially extend from the exterior surface to the lumen, and wherein each longitudinal slot of the plurality of longitudinal slots is configured to receive a respective engagement member of the plurality of engagement members.

16. The introducer system according to claim 11, wherein the anchor member includes a sleeve that radially surrounds the side wall, wherein the sleeve is made from a flexible material, the sleeve having a first end and a second end, wherein the first end is attached to the exterior surface of the side wall and the second end is slidable over the exterior surface of the side wall, wherein in the collapsed state the sleeve has a first longitudinal length and in the deployed state the sleeve has a second longitudinal length that is shorter than the first longitudinal length.

17. The introducer system according to claim 16, wherein in the deployed state, a central portion of the sleeve bulges radially away from the side wall of the tubular body.

18. The introducer system according to claim 11, wherein the distal end portion of the tubular body includes an annular ramp surface that distally terminates at the lumen at the distal end of the tubular body.

19. The introducer system according to claim 11, wherein the distal end portion of the tubular body includes a planar ramp surface that distally terminates at the distal end of the tubular body.

20. The introducer system according to claim 11, wherein the side wall of the tubular body of the implant is in a friction fit with the outer surface of the elongate cannula, the implant configured to separate from the elongate cannula.

* * * * *